United States Patent
Dubief

(10) Patent No.: US 10,178,880 B2
(45) Date of Patent: *Jan. 15, 2019

(54) AEROSOL GENERATING DEVICE WITH A CAPILLARY INTERFACE

(71) Applicant: Philip Morris Products S.A., Neuchatel (CH)

(72) Inventor: Flavien Dubief, Neuchatel (CH)

(73) Assignee: Philip Morris Products S.A., Neuchatel (CH)

(*) Notice: Subject to any disclaimer, the term of this patent is extended or adjusted under 35 U.S.C. 154(b) by 2 days.

This patent is subject to a terminal disclaimer.

(21) Appl. No.: 15/156,067

(22) Filed: May 16, 2016

(65) Prior Publication Data

US 2016/0255880 A1 Sep. 8, 2016

Related U.S. Application Data

(63) Continuation of application No. 14/363,525, filed as application No. PCT/EP2012/074513 on Dec. 5, 2012, now Pat. No. 9,364,800.

(30) Foreign Application Priority Data

Dec. 8, 2011 (EP) .................................. 11192697

(51) Int. Cl.
*B01F 3/04* (2006.01)
*B01F 3/02* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC .... B01F 3/04007; B01F 3/022; A24F 47/008; A61M 11/042; A61M 15/06
(Continued)

(56) References Cited

U.S. PATENT DOCUMENTS

| 4,848,374 A | 7/1989 | Chard |
| 4,947,875 A | 8/1990 | Brooks et al. |

(Continued)

FOREIGN PATENT DOCUMENTS

| CN | 87108020 A | 6/1988 |
| CN | 1106118 A | 8/1995 |

(Continued)

OTHER PUBLICATIONS

Notice of Allowance dated Dec. 7, 2016 in Russian Patent Application No. 2014127719 (with English language translation).
(Continued)

*Primary Examiner* — Robert A Hopkins
(74) *Attorney, Agent, or Firm* — Oblon, McClelland, Maier & Neustadt, L.L.P.

(57) ABSTRACT

There is provided an aerosol generating device comprising a storage portion (113, 501) for storing aerosol-forming substrate (115, 505). The device comprises: a vaporizer (119, 509) for heating the aerosol-forming substrate (115, 505), a capillary material (117, 507) for conveying the liquid aerosol-forming substrate (115, 505) from the storage portion (113, 501) towards the vaporizer (119, 509) by capillary action, and a porous material (201, 301, 405, 511) between the capillary material (117, 507) and the vaporizer (119, 509).

21 Claims, 3 Drawing Sheets

(51) Int. Cl.
*A24F 47/00* (2006.01)
*A61M 15/06* (2006.01)
*A61M 11/04* (2006.01)
*B01F 15/06* (2006.01)
*H05B 1/02* (2006.01)
*H05B 3/00* (2006.01)
*H05B 3/14* (2006.01)

(52) U.S. Cl.
CPC .......... *B01F 3/022* (2013.01); *B01F 3/04007* (2013.01); *B01F 15/06* (2013.01); *H05B 1/0227* (2013.01); *H05B 3/0014* (2013.01); *H05B 3/141* (2013.01); *A61M 2205/3653* (2013.01); *A61M 2205/8206* (2013.01); *B01F 2015/062* (2013.01)

(58) Field of Classification Search
USPC ............................................ 261/142, 97, 99
See application file for complete search history.

(56) References Cited

U.S. PATENT DOCUMENTS

| | | | |
|---|---|---|---|
| 5,190,060 | A | 3/1993 | Gerding et al. |
| 8,061,361 | B2 | 11/2011 | Maeder et al. |
| 2003/0075188 | A1 | 4/2003 | Adiga et al. |
| 2008/0022999 | A1 | 1/2008 | Belcastro et al. |
| 2009/0095311 | A1 | 4/2009 | Han |
| 2009/0126745 | A1 | 5/2009 | Hon |
| 2009/0272379 | A1 | 11/2009 | Thorens et al. |
| 2011/0155153 | A1 | 6/2011 | Thorens et al. |
| 2011/0209717 | A1 | 9/2011 | Han |

FOREIGN PATENT DOCUMENTS

| | | |
|---|---|---|
| CN | 1196660 A | 10/1998 |
| CN | 2662075 Y | 12/2004 |
| CN | 201067079 Y | 6/2008 |
| CN | 101977522 A | 2/2011 |
| CN | 102014677 A | 4/2011 |
| CN | 102264420 A | 11/2011 |
| CN | 104039184 B | 9/2016 |
| EA | 015651 B1 | 10/2011 |
| EP | 2 022 349 A1 | 2/2009 |
| EP | 2 110 033 A1 | 10/2009 |
| EP | 2 319 334 A1 | 5/2011 |
| EP | 2 340 729 A1 | 7/2011 |
| EP | 2 359 705 A1 | 8/2011 |
| EP | 2 404 515 A1 | 1/2012 |
| JP | 2009-537119 A | 10/2009 |
| JP | 3160708 U | 6/2010 |
| JP | 2011-518567 A | 6/2011 |
| JP | 2012-517229 A | 8/2012 |
| RU | 2 195 849 C2 | 1/2003 |
| RU | 2 297 781 C2 | 4/2007 |
| WO | 03/034847 A1 | 5/2003 |
| WO | 2009/132793 A1 | 11/2009 |
| WO | WO 2010/091593 A1 | 8/2010 |
| WO | 2011/146174 A2 | 11/2011 |

OTHER PUBLICATIONS

International Search Report and Written Opinion of the International Searching Authority dated Apr. 26, 2013, in PCT/EP2012/074513, filed Dec. 5, 2012.

Combined Office Action and Search Report dated Nov. 3, 2015 in Chinese Patent Application No. 201280066482.X (with English language translation).

Chinese Office Action with English translation dated May 18, 2018 in corresponding Chinese Patent Application No. 201610677028.8, citing documents AA and AO-AU therein (11 pages).

Korean Office Action with English translation dated Nov. 15, 2018 in corresponding Korean Patent Application No. 2014-7015642, citing documents AO therein (11 pages).

AEROSOL GENERATING DEVICE WITH A CAPILLARY INTERFACE

CROSS REFERENCE TO RELATED APPLICATIONS

This continuation application claims the benefit of priority under 35 U.S.C. § 120 from prior U.S. patent application Ser. No. 14/363,525, filed Jun. 6, 2014, which is a U.S. national phase application under 35 U.S.C. § 371 of International Application No. PCT/EP2012/074513, filed Dec. 5, 2012. This application is also based upon and claims the benefit of priority under 35 U.S.C. § 119 from European Patent Application No. 11192697.8, filed Dec. 8, 2011. The entire contents of each of the above applications are incorporated herein by reference.

The present invention relates to an aerosol generating device for heating an aerosol-forming substrate. Particularly, but not exclusively, the present invention relates to an electrically operated aerosol generating device for heating a liquid aerosol-forming substrate.

WO-A-2009/132793 discloses an electrically heated smoking system. A liquid is stored in a liquid storage portion, and a capillary wick has a first end which extends into the liquid storage portion for contact with the liquid therein, and a second end which extends out of the liquid storage portion. A heating element heats the second end of the capillary wick. The heating element is in the form of a spirally wound electric heating element in electrical connection with a power supply, and surrounding the second end of the capillary wick. In use, the heating element may be activated by the user to switch on the power supply. Suction on a mouthpiece by the user causes air to be drawn into the electrically heated smoking system over the capillary wick and heating element and subsequently into the mouth of the user.

It is an object of the present invention to improve the generation of aerosol in an aerosol generation device or system.

According to one aspect of the invention, there is provided an aerosol generating device comprising a storage portion for storing an aerosol-forming substrate; a vaporizer for heating the aerosol-forming substrate; a capillary material for conveying the aerosol-forming substrate from the storage portion towards the vaporizer by capillary action; and a porous material between the capillary material and the vaporizer.

According to another aspect of the invention, there is provided a cartridge comprising a storage portion for storing an aerosol-forming substrate; a vaporizer for heating the aerosol-forming substrate; a capillary material for conveying the aerosol-forming substrate from the storage portion towards the vaporizer by capillary action; and a porous material between the capillary material and the vaporizer.

The aerosol generating device and cartridge cooperate to provide an aerosol generating system for vaporizing the aerosol-forming substrate. The cartridge or device may comprise the storage portion for storing the aerosol-forming substrate. The vaporizer, the capillary material and the porous material may be contained in the aerosol generating device. The vaporizer, the capillary material and the porous material may also be contained in the cartridge.

According to another aspect of the invention, there is provided an aerosol generating system comprising: an aerosol generating device in cooperation with a cartridge, the cartridge or aerosol generating device comprising a storage portion for storing an aerosol-forming substrate; wherein the cartridge or aerosol generating device comprises a vaporizer for heating the aerosol-forming substrate to form an aerosol; wherein the cartridge or aerosol generating device comprises a capillary material for conveying the aerosol-forming substrate from the storage portion towards the vaporizer by capillary action; and wherein the cartridge or aerosol generating device comprises a porous material between the capillary material and the vaporizer.

For all aspects of the invention, the storage portion may be a liquid storage portion. For all aspects of the invention, the aerosol forming substrate may be a liquid aerosol forming substrate.

The aerosol-forming substrate may alternatively be any other sort of substrate, for example, a gas substrate or a gel substrate, or any combination of the various types of substrate.

The aerosol generating device or system is arranged to vaporize an aerosol-forming substrate to form the aerosol. The cartridge or aerosol generating device may include the aerosol-forming substrate or may be adapted to receive the aerosol-forming substrate. As known to those skilled in the art, an aerosol is a suspension of solid particles or liquid droplets in a gas, such as air.

Preferably, the capillary material is arranged to be in contact with aerosol-forming substrate in the storage portion. In one embodiment, liquid in the capillary material is vaporized by the heater to form a supersaturated vapour. The supersaturated vapour is mixed with and carried in the air flow. During the flow, the vapour condenses to form the aerosol and the aerosol is carried towards the mouth of a user. The liquid aerosol-forming substrate has suitable physical properties, including surface tension and viscosity, which allow the liquid to be transported through the capillary material by capillary action.

The invention provides a number of advantages. First, the porous material may provide structural support for the capillary material, to prevent the capillary material from being damaged, for example, split, bent or flattened. This is particularly true if the capillary material is a flexible material and the porous material is a rigid material. If the capillary material is protected from damage, the aerosol formation is more likely to be consistent, even over multiple uses of the aerosol generating device. Second, manufacturing costs may be reduced because the capillary material may be a simple and relatively inexpensive material. The porous material may comprise a more robust and expensive material. Thus, the more expensive material need only be used for the small porous material, and the relatively inexpensive material can be used for the bulk of the device.

The capillary material may comprise any suitable material or combination of materials which is able to convey the aerosol-forming substrate towards the vaporizer. The capillary material is preferably a porous material, but this need not be the case. The capillary material may have a fibrous or spongy structure. The capillary material preferably comprises a bundle of capillaries. For example, the capillary material may comprise a plurality of fibres or threads or other fine bore tubes. Alternatively, the capillary material may comprise sponge-like or foam-like material. The structure of the capillary material forms a plurality of small bores or tubes, through which the aerosol-forming substrate can be transported by capillary action from the storage portion towards the vaporizer. The particular preferred capillary material or materials will depend on the physical properties of the aerosol-forming substrate. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity so as to be used with different liquid physical properties. The liquid has physical properties, including but not limited to viscosity, surface tension, density, thermal conductivity, boiling point and vapour pressure, which allow the liquid to be transported through the capillary material.

The porous material may comprise any suitable material or combination of materials which is permeable to the aerosol-forming substrate and allows the aerosol-forming substrate to migrate from the capillary material to the vaporizer. The material or combination of materials is also inert with respect to the aerosol-forming substrate. The porous material may or may not be a capillary material. The porous material may comprise a hydrophilic material to improve distribution and spread of the aerosol-forming substrate. This may assist with consistent aerosol formation. The particular preferred material or materials will depend on the physical properties of the aerosol-forming substrate. Examples of suitable materials are a capillary material, for example a sponge or foam material, ceramic- or graphite-based materials in the form of fibres or sintered powders, a foamed metal or plastics material, a fibrous material, for example made of spun or extruded fibres, such as cellulose acetate, polyester, or bonded polyolefin, polyethylene, terylene or polypropylene fibres, nylon fibres or ceramic. The porous material may have any suitable porosity so as to be used with different liquid physical properties.

The porous material and capillary material preferably comprise different materials. Preferably, the capillary material and the porous material are in contact, as this provides for good transfer of liquid.

The storage portion may protect the aerosol-forming substrate from ambient air (because air cannot generally enter the liquid storage portion). The storage portion may protect the aerosol-forming substrate from light, so that the risk of degradation of the aerosol-forming substrate is significantly reduced. Moreover, a high level of hygiene can be maintained. The storage portion may not be refillable. Thus, when the aerosol-forming substrate in the storage portion has been used up, the cartridge is replaced. Alternatively, the storage portion may be refillable. In that case, the cartridge may be replaced after a certain number of refills of the storage portion. Preferably, the storage portion is arranged to hold aerosol-forming substrate for a pre-determined number of puffs.

In a preferred embodiment, the aerosol generating device is electrically operated and the vaporizer comprises an electric heater for heating the aerosol-forming substrate.

The electric heater may comprise a single heating element. Alternatively, the electric heater may comprise more than one heating element for example two, or three, or four, or five, or six or more heating elements. The heating element or heating elements may be arranged appropriately so as to most effectively heat the aerosol-forming substrate.

The at least one electric heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Del. 19898, United States of America.

Alternatively, the at least one electric heating element may comprise an infra-red heating element, a photonic source or an inductive heating element.

The at least one electric heating element may take any suitable form. For example, the at least one electric heating element may take the form of a heating blade. Alternatively, the at least one electric heating element may take the form of a casing or substrate having different electro-conductive portions, or an electrically resistive metallic tube. Alternatively, the at least one electric heating element may be a disk (end) heater or a combination of a disk heater with heating needles or rods. Alternatively, the at least one electric heating element may comprise a flexible sheet of material. Other alternatives include a heating wire or filament, for example a Nickel-chromium, platinum, tungsten or alloy wire, or a heating plate. Optionally, the heating element may be deposited in or on a rigid carrier material.

The at least one electric heating element may comprise a heat sink, or heat reservoir comprising a material capable of absorbing and storing heat and subsequently releasing the heat over time to heat the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material. Other suitable materials which release heat via a reversible phase change include paraffin, sodium acetate, naphthalene, wax, polyethylene oxide, a metal, metal salt, a mixture of eutectic salts or an alloy.

The heat sink may be arranged such that it is directly in contact with the aerosol-forming substrate being conveyed from the storage portion and can transfer the stored heat directly to the aerosol-forming substrate. Alternatively, the heat stored in the heat sink or heat reservoir may be transferred to the aerosol-forming substrate by means of a heat conductor, such as a metallic tube.

The at least one heating element may heat the aerosol-forming substrate by means of conduction. The heating element may be at least partially in contact with the aerosol-forming substrate. Alternatively, the heat from the heating element may be conducted to the aerosol-forming substrate by means of a heat conductor.

Alternatively, the at least one heating element may transfer heat to the incoming ambient air that is drawn through the aerosol generating device during use, which in turn heats the aerosol-forming substrate by convection. The ambient air may be heated before passing through the aerosol-forming substrate. Alternatively, the ambient air may be first drawn through the aerosol-forming substrate and then heated.

However, the invention is not limited to heater vaporizers but may be used in aerosol generating devices and systems in which the vapour and resulting aerosol is generated by a mechanical vaporizer, for example but not limited to a piezo vaporizer or an atomizer using pressurized liquid.

If the vaporizer comprises an electric heater, preferably, the porous material comprises a heat-resistant material. Preferably, the electrical energy is supplied to the heating element or elements until the heating element or elements reach a temperature of between approximately 200° C. and 440° C. This is in contrast to conventional cigarettes in which the combustion of tobacco and cigarette wrapper may reach 800° C. Thus, the term "heat-resistant" in this specification refers to a material which is able to tolerate temperatures of more than approximately 200° C., or more preferably more than approximately 250° C., or even more preferably up to approximately 440° C., without noticeably degrading. An example of a suitable material is ceramic.

Thus, a further advantage of this embodiment of the invention is that the porous material can prevent heat damage to the capillary material. The porous material may also provide an improved, even heat distribution. This may assist with consistent aerosol formation. Suitable heat-resistant materials may be expensive. But, the capillary material only needs to tolerate the temperatures at the capillary-porous interface, because the porous material provides a heat-resistant barrier between the capillary material and the electric heater. These temperatures are lower than those at the heating element or elements. Thus, a smaller amount of potentially expensive heat-resistant material can be used. This reduces manufacturing costs. The heat-resistant material provides insulation between the heater and the capillary material.

Preferably, the porous material comprises an electrically insulating material. If the vaporizer comprises an electric heater this prevents any short circuit of the heating elements.

In one embodiment, the porous material simply comprises a layer of porous material between the vaporizer and the capillary material. In an alternative embodiment, the porous material comprises a coating of porous material over the vaporizer. In an alternative embodiment, the vaporizer is situated within a porous member, the porous member comprising the porous material. Thus, the vaporizer is located inside the porous member, and the portion of the porous member between the vaporizer and the capillary material forms the porous material. The vaporizer and the porous member may be integrally formed. The term "integrally formed" refers to both the vaporizer and the porous member being manufactured together in one piece.

In a particularly preferred embodiment, the aerosol generating device is electrically operated, the vaporizer comprises an electric heater for heating the aerosol-forming substrate, and the electric heater and a porous member, including the porous material, are integrally formed. In one arrangement, the electric heater is located inside the porous member such that, when the porous member is adjacent the capillary material, the portion of the porous member between the electric heater and the capillary material forms the porous material. In that embodiment, the porous member comprises heat-resistant material.

In one embodiment, the capillary material comprises an elongate capillary body for conveying the liquid aerosol-forming substrate from the liquid storage portion towards the vaporizer, the capillary body having a first end extending into the liquid storage portion and a second end opposite the first end, wherein the vaporizer is arranged to vaporize the liquid aerosol-forming substrate in the second end of the capillary body.

In this embodiment, in use, liquid is transferred from the liquid storage portion by capillary action from the first end of the capillary body towards the second end of the capillary body. The porous material is provided between the second end of the capillary body and the vaporizer. Liquid in the second end of the capillary body and in the porous material is vaporized to form the supersaturated vapour. The capillary body may have the form of a wick. The capillary body may comprise fibres or threads generally aligned in the longitudinal direction of the aerosol generating device or system. Alternatively, the capillary body may comprise sponge-like or foam-like material formed into a rod shape. The rod shape may extend along the longitudinal direction of the aerosol generating device or system.

In a preferred embodiment, the capillary material comprises an elongate capillary body for conveying the liquid aerosol-forming substrate from the liquid storage portion, the capillary body having a first end extending into the liquid storage portion and a second end opposite the first end, and the vaporizer comprises an electric heater arranged to heat the liquid aerosol-forming substrate in the second end of the capillary body. The porous material is provided between the second end of the capillary body and the electric heater. When the heater is activated, liquid at the second end of the capillary body and in the porous material is vaporized by the heater to form the supersaturated vapour.

In one embodiment, the porous material comprises a sleeve of porous material substantially surrounding the second end of the capillary body.

The sleeve of porous material may surround the second end of the capillary body sufficiently such that the capillary body is not in contact with the vaporizer. This is particularly important when the vaporizer comprises an electric heater, since the capillary material may not be heat-resistant. The sleeve of porous material may provide protection and support for the capillary body. The porous sleeve does not need to surround the entire capillary body, as long as the porous sleeve prevents any contact between the capillary body and the vaporizer which may damage the capillary body.

Alternatively, or additionally, the porous material may comprise a cap of porous material substantially covering the second end of the capillary body.

The cap of porous material may cover the second end of the capillary body sufficiently such that the capillary body is not in contact with the vaporizer. This is particularly important when the vaporizer comprises an electric heater, since the capillary material may not be heat-resistant. The cap of porous material may provide protection and support for the capillary body. For example, if the capillary body comprises a plurality of fibres or threads, the cap of porous material may reduce the likelihood of splitting or breaking of the capillary body. The porous cap does not need to cover the entire capillary body, as long as the porous cap prevents any contact between the capillary body and the vaporizer which may damage the capillary body.

In one particularly preferred embodiment, the cartridge comprises a mouthpiece; an electric power supply and electric circuitry are arranged in the device; the capillary material comprises an elongate capillary body for conveying the aerosol-forming substrate from the liquid storage portion, the capillary body having a first end extending into the storage portion and a second end opposite the first end; the vaporizer comprises an electric heater, connectable to the electric power supply, for heating the aerosol-forming substrate in the second end of the capillary body; and the storage portion, capillary body and electric heater are arranged in the cartridge.

The storage portion, and optionally the capillary body and the heater, may be removable from the aerosol generating system as a single component.

In one embodiment, the storage portion includes an interior passageway, the vaporizer extends through at least part of the interior passageway in the storage portion, and the capillary material comprises a capillary interface at least partially lining the interior passageway.

In this embodiment, in use, liquid is transferred from the liquid storage portion by capillary action through the capillary interface lining the interior passageway. The inner face of the capillary interface is preferably in contact with the liquid aerosol-forming substrate in the liquid storage portion. The porous material is provided between the outer face of the capillary interface and the vaporizer. Liquid near the outer face of the capillary interface and in the porous material is vaporized to form the supersaturated vapour. The capillary interface may comprise any suitable capillary material formed into a tube shape. The tube of capillary material may extend along all of or part of the length of the interior passageway in the liquid storage portion.

In a preferred embodiment, the liquid storage portion has an interior passageway, the vaporizer comprises an electric heater extending through at least part of the interior passageway in the liquid storage portion and the capillary material comprises a capillary interface at least partially lining the interior passageway, wherein the electric heater is arranged to heat the liquid aerosol-forming substrate near an outer face of the capillary interface. The porous material is provided between the outer face of the capillary interface and the electric heater. When the heater is activated, the liquid near the outer face of the capillary interface is vaporized by the heater to form the supersaturated vapour.

In that embodiment, preferably, the porous material comprises a tube of porous material inside the capillary interface, lining or partially lining the interior passageway of the liquid storage portion.

The tube of porous material may be positioned such that the outer face of the capillary interface is not in contact with the vaporizer. This is particularly important when the vaporizer comprises an electric heater, since the capillary material of the capillary interface may not be heat-resistant. The porous material only needs to act as a barrier in the vicinity of the vaporizer.

In one particularly preferred embodiment, the cartridge comprises a mouthpiece; an electric power supply and electric circuitry are arranged in the device; the liquid storage portion has an interior passageway; the vaporizer comprises an electric heater for heating the liquid aerosol-forming substrate, connectable to the electric power supply and extending through at least part of the interior passageway in the liquid storage portion; the capillary material comprises a capillary interface at least partially lining the interior passageway; and the liquid storage portion, capillary interface and electric heater are arranged in the cartridge.

The liquid storage portion, and optionally the capillary interface and the heater, may be removable from the aerosol generating system as a single component.

The liquid aerosol-forming substrate preferably has physical properties, for example boiling point and vapour pressure, suitable for use in the device, cartridge or system. If the boiling point is too high, it may not be possible to vaporize the liquid but, if the boiling point is too low, the liquid may vaporize too readily. The liquid preferably comprises a tobacco-containing material comprising volatile tobacco flavour compounds which are released from the liquid upon heating. Alternatively, or in addition, the liquid may comprise a non-tobacco material. The liquid may include aqueous solutions, non-aqueous solvents such as ethanol, plant extracts, nicotine, natural or artificial flavours or any combination of these. Preferably, the liquid further comprises an aerosol former. Examples of suitable aerosol formers are glycerine and propylene glycol.

The aerosol generating device or cartridge may comprise at least one air inlet. The aerosol generating device or cartridge may comprise at least one air outlet. The aerosol generating device or cartridge may comprise an aerosol forming chamber between the air inlet and air outlet so as to define an air flow route from the air inlet to the air outlet via the aerosol forming chamber, so as to convey the aerosol to the air outlet and into the mouth of a user. In embodiments in which the liquid storage portion comprises an interior passageway, preferably the air flow route from the air inlet to the air outlet passes through the interior passageway. The aerosol forming chamber simply assists or facilitates the generation of the aerosol.

The aerosol generating device may be electrically operated and may further comprise an electric power supply. The aerosol generating device may further comprise electric circuitry. In one embodiment, the electric circuitry comprises a sensor to detect air flow indicative of a user taking a puff. In that case, preferably, the electric circuitry is arranged to provide an electric current pulse to the vaporizer when the sensor senses a user taking a puff. Preferably, the time-period of the electric current pulse is pre-set, depending on the amount of liquid desired to be vaporized. The electric circuitry is preferably programmable for this purpose. Alternatively, the electric circuitry may comprise a manually operable switch for a user to initiate a puff. The time-period of the electric current pulse is preferably pre-set depending on the amount of liquid desired to be vaporized. The electric circuitry is preferably programmable for this purpose.

Preferably, the device or cartridge or system comprises a housing. Preferably, the housing is elongate. If the aerosol generating device or cartridge includes an elongate capillary body, the longitudinal axis of the capillary body and the longitudinal axis of the housing may be substantially parallel. In one embodiment, the housing includes a removable insert comprising the liquid storage portion, the capillary body and the heater. In that embodiment, those parts may be removable from the housing as a single component. This may be useful for refilling or replacing the storage portion, for example.

The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

Preferably, the aerosol generating device and cartridge are portable, both individually and in cooperation. Preferably, the aerosol generating device is reusable by a user. Preferably, the cartridge is disposable by a user, for example when there is no more liquid contained in the liquid storage portion. The aerosol generating device and cartridge may cooperate to form an aerosol generating system which is a smoking system and which may have a size comparable to a conventional cigar or cigarette. The smoking system may have a total length between approximately 30 mm and approximately 150 mm. The smoking system may have an external diameter between approximately 5 mm and approximately 30 mm.

Preferably, the aerosol generating system is an electrically operated smoking system.

According to the invention, there is also provided an aerosol generating system comprising: a storage portion for storing an aerosol-forming substrate; a vaporizer for heating the aerosol-forming substrate to form an aerosol; a capillary material for conveying the aerosol-forming substrate from the storage portion towards the vaporizer by capillary action; and a porous material between the capillary material and the vaporizer. In this embodiment, the aerosol generating system does not comprise a separate device and cartridge.

In a particularly preferred embodiment, the capillary material comprises polypropylene and the porous material comprises a ceramic material, for example, alumina (aluminium oxide).

Features described in relation to one aspect of the invention may be applicable to another aspect of the invention.

The invention will be further described, by way of example only, with reference to the accompanying drawings, of which:

Figure 1:
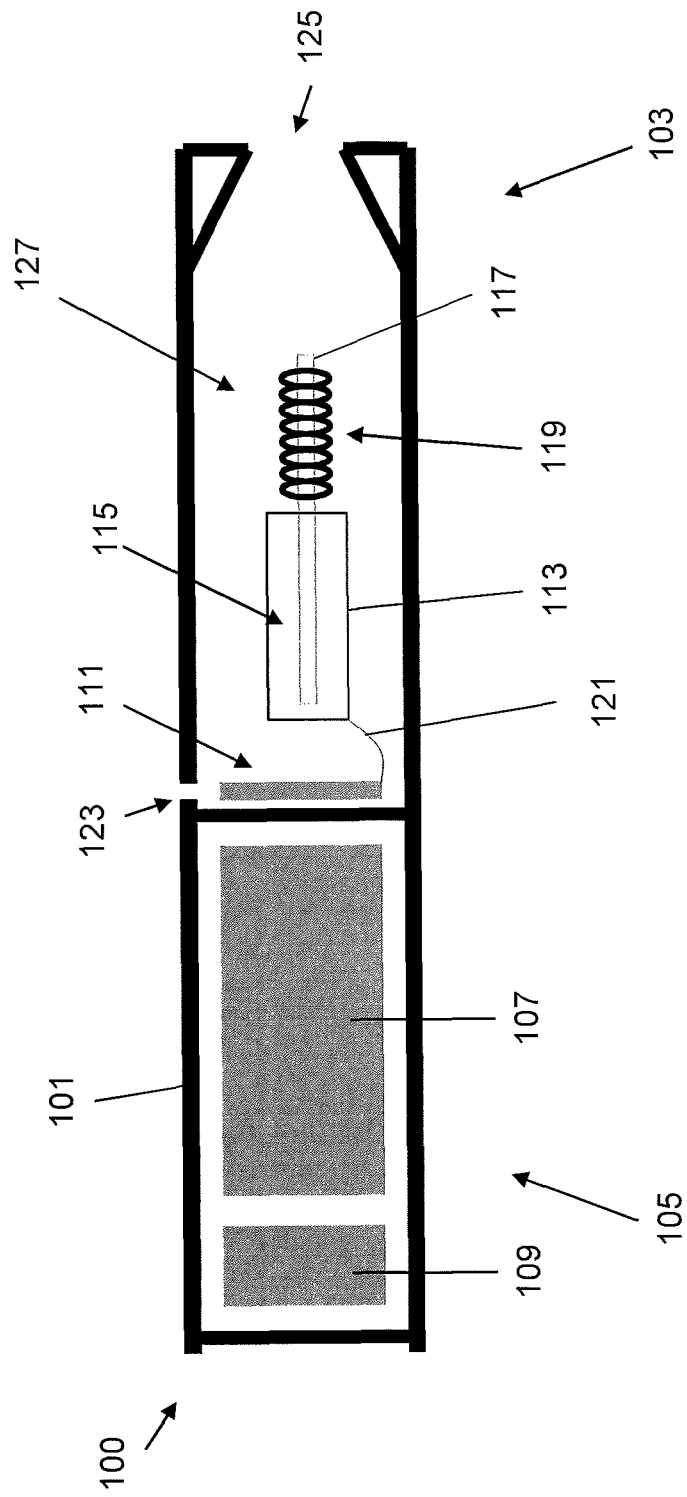
FIG. 1 shows one example of an aerosol generating system

FIG. 1 shows one example of an aerosol generating system. Although not explicitly shown in FIG. 1, the aerosol generating system comprises an aerosol generating device, which is preferably reusable, in cooperation with a cartridge, which is preferably disposable. In FIG. 1, the system is an electrically operated smoking system. The smoking system 100 of FIG. 1 comprises a housing 101 having a first end which is the cartridge 103 and a second end which is the device 105. In the device, there is provided an electric power supply in the form of battery 107 and electric circuitry in the form of hardware 109 and puff detection system 111. In the cartridge, there is provided a storage portion 113 containing liquid 115, capillary material in the form of an elongate capillary body 117 and a vaporizer in the form of heater 119.

Note that the heater is only shown schematically in FIG. 1. In the exemplary embodiment shown in FIG. 1, one end of capillary body 117 extends into liquid storage portion 113 and the other end of capillary body 117 is surrounded by the heater 119. The heater is connected to the electric circuitry via connections 121, which may pass along the outside of liquid storage portion 113 (not shown in FIG. 1). The housing 101 also includes an air inlet 123, an air outlet 125 at the cartridge end, and an aerosol forming chamber 127.

In use, operation is as follows. Liquid 115 is conveyed by capillary action from the liquid storage portion 113 from the end of the capillary body 117 which extends into the liquid storage portion to the other end of the capillary body which is surrounded by heater 119. When a user draws on the air outlet 125, ambient air is drawn through air inlet 123. In the arrangement shown in FIG. 1, the puff detection system 111 senses the puff and activates the heater 119. The battery 107 supplies electrical energy to the heater 119 to heat the end of the capillary body 117 surrounded by the heater. The liquid in that end of the capillary body 117 is vaporized by the heater 119 to create a supersaturated vapour. At the same time, the liquid being vaporized is replaced by further liquid moving along the capillary body 117 by capillary action. (This is sometimes referred to as "pumping action".) The supersaturated vapour created is mixed with and carried in the air flow from the air inlet 123. In the aerosol forming chamber 127, the vapour condenses to form an inhalable aerosol, which is carried towards the outlet 125 and into the mouth of the user.

In the embodiment shown in FIG. 1, the hardware 109 and puff detection system 111 are preferably programmable. The hardware 109 and puff detection system 111 can be used to manage the aerosol generating operation.

FIG. 1 shows one example of an aerosol generating system according to the present invention. Many other examples are possible, however. The aerosol generating system simply needs to include or receive a liquid aerosol-forming substrate contained in a storage portion, a vaporizer for heating the liquid aerosol-forming substrate, a capillary material for conveying the liquid aerosol-forming substrate towards the vaporizer and some sort of porous material (to be described below with reference to FIGS. 2 to 6) between the capillary material and the vaporizer. For example, the system need not be electrically operated. For example, the system need not be a smoking system. In addition, the system may not include a heater, in which case another device may be included to vaporize the liquid aerosol-forming substrate. For example, the configuration of the capillary material may be different. For example, a puff detection system need not be provided. Instead, the system could operate by manual activation, for example the user operating a switch when a puff is taken. For example, the overall shape and size of the housing could be altered.

As discussed above, according to the invention, there is provided a porous material between the capillary material and the vaporizer. Embodiments of the invention, including the porous material, will now be described with reference to FIGS. 2 to 6. The embodiments are based on the example shown in FIG. 1, although are applicable to other embodiments. Note that FIGS. 1 to 5 are schematic in nature. In particular, the components shown are not necessarily to scale either individually or relative to one another.

Figure 2:
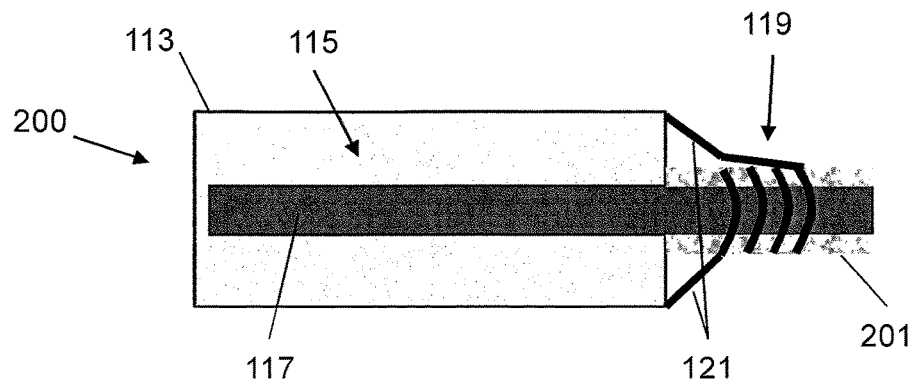
FIG. 2 is a schematic cross-sectional view of a first embodiment of a cartridge for use with an aerosol generating device to produce an aerosol generating system like that shown in FIG. 1.

FIG. 2 is a schematic view of a first embodiment of a cartridge for use with an aerosol generating device to produce an aerosol generating system like that shown in FIG. 1. The cartridge 200 includes a storage portion 113, capillary body 117 and heater 119. The liquid storage portion 113 contains liquid aerosol-forming substrate 115. In FIG. 2, the heater 119 is in the form of a heating coil, connected to electric circuitry (not shown) via electrical connections 121. The heater 119 and electrical connections 121 are shown schematically in FIG. 2 and the electrical connections may pass along the outside of liquid storage portion 113 although this is not shown in FIG. 2. There is further provided a porous material in the form of porous sleeve 201 surrounding the end of the capillary body 117 which protrudes from the liquid storage portion 113.

The porous sleeve 201 provides structural support for the capillary body 117. Preferably, the porous sleeve 201 comprises a rigid material. Thus, the porous sleeve 201 prevents or reduces the likelihood of the capillary body 117 becoming damaged, for example split, bent or flattened. The porous sleeve 201 may be retained in position by slotting into the housing or another part of the aerosol generating device or cartridge, when the cartridge is assembled with the aerosol generating device. The porous sleeve 201 preferably comprises a heat-resistant material which can protect the capillary body 117 from potential heat damage from the heater. Thus, the porous sleeve acts as a heat barrier. The porous sleeve 201 may also improve the heat distribution. The porous sleeve 201 may become more efficient at liquid transfer, as the aerosol generating system heats up. In FIG. 2, the size of the porous sleeve 201 is small compared with the size of the capillary body 117. Thus, only a small amount of heat-resistant material may be required. Since the heat-resistant material may be expensive, this may reduce manufacturing costs. In this embodiment, the porous sleeve 201 comprises an electrically insulating material so as not to cause a short circuit across the heater coils.

In FIG. 2, the porous sleeve 201 does not cover the terminal end of the capillary body 117. Although, in FIG. 2, the porous sleeve 201 surrounds the entire end of the capillary body which protrudes from the liquid storage portion 113, the porous sleeve may simply cover the capillary body in the vicinity of the heater 119, so as to prevent heat damage to the capillary body 117. The required diameter of the porous sleeve 201 will depend on the size of the capillary body 117 and liquid storage portion 113. The required length of the porous sleeve 201 will depend on the size of the heater 119 which will, in turn, depend on the amount of liquid desired to be vaporized. The required thickness of the porous sleeve 201 will depend on the insulating properties and porosity required.

Figure 3:
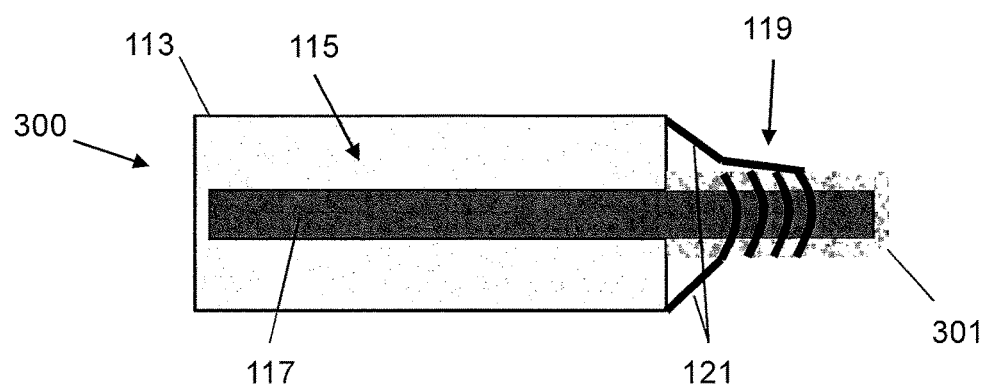
FIG. 3 is a schematic cross-sectional view of a second embodiment of a cartridge for use with an aerosol generating device to produce an aerosol generating system like that shown in FIG. 1.

FIG. 3 is a schematic view of a second embodiment of a cartridge for use with an aerosol generating device to produce an aerosol generating system like that shown in FIG. 1.

The cartridge 300 includes a storage portion 113, capillary body 117 and heater 119. The liquid storage portion 113 contains liquid aerosol-forming substrate 115. As in FIG. 2, in FIG. 3, the heater 119 is in the form of a heating coil, connected to electric circuitry (not shown) via electrical connections 121. The heater 119 and electrical connections 121 are shown schematically in FIG. 3 and the electrical connections may pass along the outside of liquid storage portion 113 although this is not shown. There is further provided a porous material in the form of porous cap 301 surrounding the end of the capillary body 117 which protrudes from the liquid storage portion 113 and covering the terminal end of the capillary body 117.

The porous cap 301 provides structural support for the capillary body 117. Preferably, the porous cap 301 comprises a rigid material. Thus, the porous cap 301 prevents or reduces the likelihood of the capillary body 117 becoming damaged, for example split, bent or flattened. In particular, because the terminal end of the capillary body 117 is covered, the chance of the capillary material splitting is substantially reduced. The porous cap 301 may be retained in position by slotting into the housing or another part of the aerosol generating device or cartridge, when the cartridge is assembled with the aerosol generating device. The porous cap 301 preferably comprises a heat-resistant material which can protect the capillary body 117 from potential heat damage from the heater. Thus, the porous cap acts as a heat barrier. The porous cap 301 may also improve the heat distribution. The porous cap 301 may become more efficient at liquid transfer, as the aerosol generating system heats up. In FIG. 3, the size of the porous cap 301 is small compared with the size of the capillary body 117. Thus, only a small amount of heat-resistant material may be required. Since the heat-resistant material may be expensive, this may reduce manufacturing costs. In this embodiment, the porous cap 301 comprises an electrically insulating material so as not to cause a short circuit across the heater coils.

In FIG. 3, the porous cap 301 surrounds the entire end of the capillary body which protrudes from the liquid storage portion 113 and also covers the terminal end of the capillary body 117. However, the porous cap may simply cover the capillary body in the vicinity of the heater 119, so as to prevent heat damage to the capillary body 117. The required diameter of the porous cap 301 will depend on the size of the capillary body 117 and liquid storage portion 113. The required length of the porous cap 301 will depend on the size of the heater 119 which will, in turn, depend on the amount of liquid desired to be vaporized. The required thickness of the porous cap 301 will depend on the insulating properties and porosity required.

Figure 4:
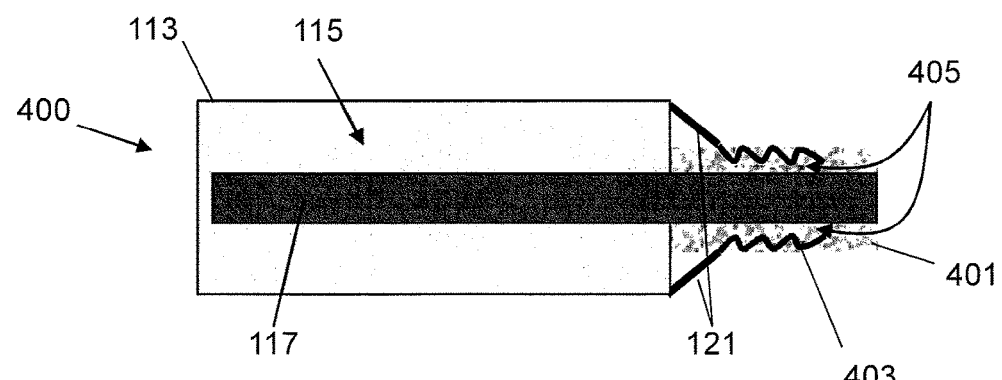
FIG. 4 is a schematic cross-sectional view of a third embodiment of a cartridge for use with an aerosol generating device to produce an aerosol generating system like that shown in FIG. 1.

FIG. 4 is a schematic view of a third embodiment of a cartridge for use with an aerosol generating device to produce an aerosol generating system like that shown in FIG. 1. The cartridge 400 includes liquid storage portion 113 and capillary body 117 and, as in FIGS. 2 and 3, the liquid storage portion 113 contains liquid aerosol-forming substrate 115. There is further provided a porous member 401 surrounding the end of the capillary body 117 which protrudes from the liquid storage portion 113. A heating blade or blades 403 are located within the porous member 401. The portion of the porous member 401 between the heater blade or blades 403 and the capillary body 117 forms a porous material 405. The heater blades 403 are connected to electric circuitry (not shown) via electrical connections 121. The heater blades 403 and electrical connections 121 are shown schematically in FIG. 4 and the electrical connections may pass along the outside of liquid storage portion 113 although this is not shown.

The porous member 401 provides structural support for the capillary body 117. Preferably, the porous member 401 comprises a rigid material. Thus, the porous member 401 prevents or reduces the likelihood of the capillary body 117 becoming damaged, for example split, bent or flattened. The porous member 401 may be retained in position by slotting into the housing or another part of the aerosol generating device or cartridge, when the cartridge is assembled with the aerosol generating device. The porous member 401 preferably comprises a heat-resistant material which can protect the capillary body 117 from potential heat damage from the heater blade or blades 403. Thus, the portion 405 of the porous member 401 between the heater blades 403 and the capillary body 117 acts as a heat barrier. The porous member 401 may also improve the heat distribution. The porous member 401 may become more efficient at liquid transfer, as the aerosol generating system heats up. In FIG. 4, the size of the porous member 401 is small compared with the size of the capillary body 117. Thus, only a small amount of heat-resistant material may be required. Since the heat-resistant material may be expensive, this may reduce manufacturing costs. In this embodiment, the porous member 401 comprises an electrically insulating material so as not to cause a short circuit across the heater blade or blades.

In FIG. 4, the porous member 401 surrounds the entire end of the capillary body which protrudes from the liquid storage portion 113. However, the porous member 401 may be shorter than the exposed portion of the capillary body. In FIG. 4, the porous member 401 does not cover the terminal end of the capillary body 117, although it is possible for the porous member 401 to cover the terminal end of the capillary body, like the embodiment shown in FIG. 3. The heating blades 403 may take any form suitable for heating the liquid aerosol-forming substrate in the capillary body 117 and the porous member 401. The required diameter of the porous member 401 will depend on the size of the capillary body 117 and liquid storage portion 113. The required length of the porous member 401 will depend on the size and shape of the heater blades, which will, in turn, depend on the amount of liquid desired to be vaporized. The required thickness of the porous member 401, in particular the porous material 405, will depend on the insulating properties and porosity required. Preferably, the heating blades 403 and the porous member 401 are integrally formed, that is, manufactured together in one piece. This simplifies manufacture.

Figure 5:
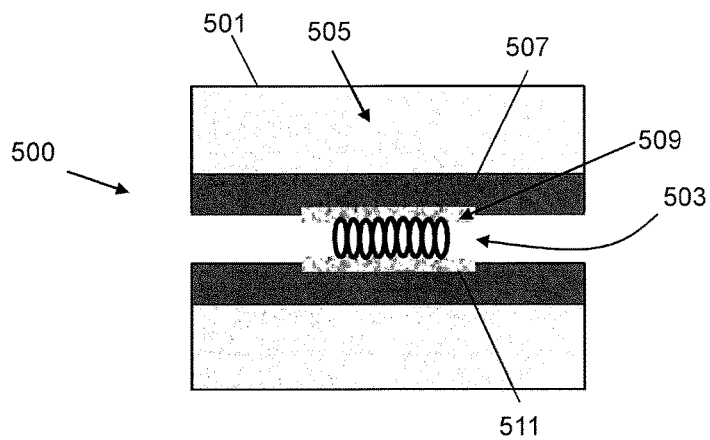
FIG. 5 is a schematic cross-sectional view of a fourth embodiment of a cartridge for use with an aerosol generating device to produce an aerosol generating system like that shown in FIG. 1.

FIG. 5 is a schematic view of a fourth embodiment of a cartridge for use with an aerosol generating device to produce an aerosol generating system like that shown in FIG. 1. However, the embodiment shown in FIG. 5 has a very different form from the cartridges shown in FIGS. 1 to 4. In FIG. 5, the cartridge 500 comprises a storage portion 501, which is in the form of a container having an interior passageway 503. In FIG. 5, the liquid storage portion 501 contains liquid aerosol-forming substrate 505. Preferably, the cartridge cooperates snugly with the aerosol generating device, and the interior passageway 503 forms part of the air flow route for air flowing into the air inlet or inlets 123 (see FIG. 1) towards the air outlet 125 (see FIG. 1). The interior passageway 503 is lined or partially lined with capillary material in the form of a capillary interface 507. A heater 509 extends through the interior passageway 503. In FIG. 5, the heater 509 is in the form of a heating coil. The heating coil is connected to electric circuitry (not shown) via electrical connections (also not shown). There is further provided a porous material in the form of porous tube 511 lining or partially lining the interior passageway 503 and providing a barrier between the heater 509 and the capillary interface 507. Preferably, the heater 509 is in contact with the porous tube 511 and preferably the porous tube 511 is in contact with the capillary interface 507. This ensures good transfer of the liquid aerosol-forming substrate from the liquid storage portion 501 towards the heater 509.

Operation of the embodiment shown in FIG. 5 is similar to operation of the embodiments shown in FIGS. 1 to 4. In use, liquid aerosol-forming substrate 505 is conveyed by capillary action from the liquid storage portion 501 from the side of the capillary interface 507 in contact with the liquid to the side of the capillary interface 507 in contact with the porous tube 511. When a user draws on the air outlet, ambient air is drawn through the interior passageway 503 and the heater 509 is activated. The heater 509 heats the liquid aerosol-forming substrate 505 in the capillary interface 507 and in the porous tube 511, and the porous tube 511 protects the capillary interface 507 from heat damage. The liquid is vaporized by the heater to form a supersaturated vapour and, at the same time, the liquid being vaporized is replaced by further liquid moving through the capillary interface 507 and into the porous tube 511. The supersaturated vapour is mixed with and carried in the air flow through the interior passageway and into the mouth of the user.

The porous tube 511 provides structural support for the capillary interface 507. Preferably, the porous tube 511 comprises a rigid material. Thus the porous tube 511 prevents or reduces the likelihood of the capillary interface 507 becoming damaged, for example, split or deformed. The porous tube 511 may also help to ensure that the capillary interface 507 stays in position lining the interior passageway 503. The porous tube 511 preferably comprises a heat-resistant material which can protect the capillary interface 507 from potential heat damage from the heater 509. Thus, the porous tube 511 acts as a heat barrier. The porous tube 511 may also improve the heat distribution. The porous tube 511 may become more efficient at liquid transfer, as the aerosol generating system heats up. In FIG. 5, the length of the porous tube 511 is small compared with the length of the capillary interface 507. Thus, only a small amount of heat-resistant material may be required. Since the heat-resistant material may be expensive, this may reduce manufacturing costs. In this embodiment, the porous tube 511 may comprise an electrically insulating material so as not to cause a short circuit across the heater coils. In FIG. 5, the porous tube 511 does not extend along the length of the liquid storage portion 501 and capillary interface 507, although this is possible. The porous tube 511 may extend along any length of the liquid storage portion 501 and capillary interface 507 as long as it provides a barrier for the capillary interface 507 in the vicinity of the heater 509. The required diameter of the porous tube 511 will depend on the size of the interior passageway 503 of the liquid storage portion 501. The required length of the porous tube 511 will depend on the size of the heater 509 which will, in turn, depend on the amount of liquid desired to be vaporized. The required thickness of the porous tube 511 will depend on the insulating properties and porosity required.

The embodiments illustrated in FIGS. 2 to 5 include a capillary material and a porous material. The capillary material may comprise any suitable material or combination of materials which is able to convey the liquid aerosol-forming substrate towards the heater. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity so as to be used with different liquid physical properties.

The porous material may comprise any suitable material or combination of materials which is permeable to the liquid aerosol-forming substrate and allows the liquid aerosol-forming substrate to migrate from the capillary material to the heater. The porous material may comprise a material which is inherently porous, for example a ceramic material such as alumina (aluminium oxide). Alternatively, the porous material may comprise a material with a plurality of manufactured small holes, to allow migration of the liquid aerosol-forming substrate to the vaporizer. The porous material may comprise a hydrophilic material to improve distribution and spread of the liquid aerosol-forming substrate. The particular preferred material or materials will depend on the physical properties of the liquid aerosol-forming substrate. Examples of suitable materials are a capillary material, for example a sponge or foam material, ceramic- or graphite-based materials in the form of fibres or sintered powders, a foamed metal or plastics material, a fibrous material, for example made of spun or extruded fibres, such as cellulose acetate, polyester, or bonded polyolefin, polyethylene, terylene or polypropylene fibres, nylon fibres or ceramic. The porous material may have any suitable porosity so as to be used with different liquid physical properties. In the embodiments illustrated in FIGS. 2 to 5, the porous material is a separate component. However, other forms for the porous material may be envisaged. For example, the porous material may comprise a porous coating over the heater or part of the heater. Other embodiments are also possible.

FIGS. 2 to 5 show examples of cartridges for use with an aerosol generating device according to the present invention. Other examples are possible. Preferably, the cartridge is disposable and is arranged to cooperate with an aerosol generating device which may be reusable. The cartridge may be refilled or replaced when the liquid is used. Thus, when the liquid aerosol-forming substrate in the cartridge has been used up, the cartridge may be disposed of and replaced with a new cartridge, or the empty cartridge may be refilled. However, the aerosol generating device may not be designed to operate in conjunction with a separate cartridge. Instead, the aerosol generating device may include or receive a liquid aerosol-forming substrate in a storage portion and comprise the vaporizer for heating the liquid aerosol-forming substrate, the capillary material for conveying the liquid aerosol-forming substrate towards the vaporizer and the porous material between the vaporizer and the capillary material. That is to say, the aerosol generating device may comprise all the components described in relation to the cartridge. Additionally, the aerosol generating device may comprise an electric power supply and electric circuitry.

In FIGS. 1 to 5, the vaporizer comprises an electric heater and the porous material protects the capillary material from heat damage. The porous material also improves heat distribution which results in more consistent aerosol formation. In one preferred embodiment, the capillary material comprises polypropylene and the porous material comprises ceramic. The inventors of the present invention have compared the heat distribution patterns across the polypropylene capillary material and ceramic barrier with the heat distribution patterns in arrangements without a porous material. If the capillary material is polypropylene, and no porous material is provided, it has been found that, after only 2 s of heating, the temperatures in the capillary material exceed the melting temperature of polypropylene. The temperatures are not homogeneous, with steep temperature gradients and hot spots. Thus, even though polypropylene would be a convenient (and relatively inexpensive) material to use for the capillary material, it cannot be used (without a porous material) since the polypropylene would melt. On the other hand, if the capillary material is ceramic, and no porous material is provided, it has been found that, after only 2 s of heating, the temperatures in the capillary material do not exceed the melting temperature of the ceramic (which is much higher than that of polypropylene). Thus, ceramic would be an ideal material for the capillary material, but it is relatively expensive. According to one embodiment of the invention, the capillary material comprises polypropylene, and a ceramic porous material is provided. In that embodiment, it has been found that the temperature in the polypropylene capillary material is considerably lower than that found with a polypropylene capillary material alone, because the ceramic barrier protects the capillary material. The temperatures have also been found to be reasonably homogeneous. Thus, the bulk of the required material can be the (relatively inexpensive) polypropylene, but the polypropylene can be protected from temperatures above its melting point by the ceramic barrier.

Figure 6:
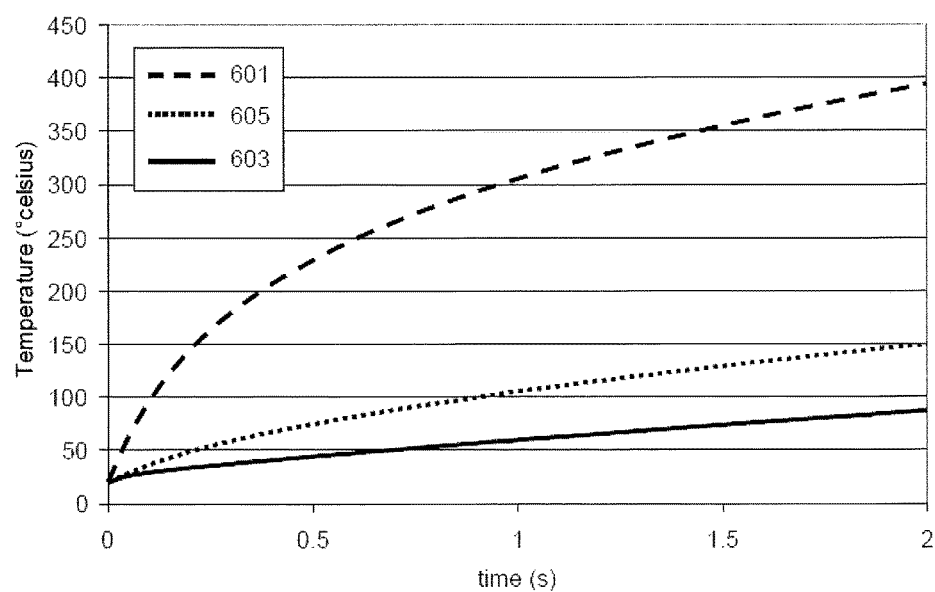
FIG. 6 is a graph of heating time versus temperature for three configurations of aerosol generating system.

FIG. 6 is a graph of heating time (s) versus temperature (° C.) for each of the three configurations described above. FIG. 6 shows the maximum temperature reached after 2 s of heating. Curve 601 is the heating curve for the configuration including a polypropylene capillary material and no porous material. The temperature reached in the capillary material after 2 s of heating is nearly 400° C. Curve 603 is the heating curve for the configuration including a ceramic capillary material and no porous material. The temperature reached in the capillary material after 2 s of heating is less than 100° C. Curve 605 is the heating curve for the embodiment of the invention including a polypropylene capillary material together with a ceramic barrier. The temperature reached in the capillary material is only approximately 150° C. Thus, the embodiment of the invention has significantly reduced the maximum temperature reached in the capillary material, whilst avoiding the need for large amounts of expensive ceramic material.

Thus, according to the invention, the aerosol generating device or cartridge or system includes a porous material between the capillary material and the vaporizer. The porous material provides structural support to the capillary material, may reduce manufacturing costs and, if the vaporizer comprises a heater, may protect the capillary material from heat damage. Embodiments of the porous material have been described with reference to FIGS. 2 to 6. Features described in relation to one embodiment may also be applicable to another embodiment.

The invention claimed is:

1. An aerosol generating device, comprising
an aerosol-forming substrate;
a vaporizer configured to heat the aerosol-forming substrate;
a capillary material configured to convey the aerosol-forming substrate towards the vaporizer by capillary action; and
a porous material between the capillary material and the vaporizer,
wherein the vaporizer is disposed inside a porous member, and
wherein a portion of the porous member disposed between the vaporizer and the capillary material forms the porous material.

2. The aerosol generating device according to claim 1, wherein the aerosol generating device is electrically operated and the vaporizer comprises an electric heater configured to heat the aerosol-forming substrate.

3. The aerosol generating device according to claim 1, wherein the porous material comprises a heat-resistant material.

4. The aerosol generating device according to claim 2, wherein the electric heater is configured to reach a temperature of between 200 degrees Celsius and 440 degrees Celsius.

5. The aerosol generating device according to claim 1, wherein the porous material is ceramic.

6. The aerosol generating device according to claim 1, wherein the porous material and the capillary material comprise different materials.

7. The aerosol generating device according to claim 1, wherein the vaporizer and the porous member are integrally formed.

8. The aerosol generating device according to claim 1, further comprising a storage portion configured to store the aerosol-forming substrate, the storage portion being refillable.

9. The aerosol generating device according to claim 1, further comprising a storage portion configured to store the aerosol-forming substrate, the storage portion comprising an interior passageway.

10. The aerosol generating device according to claim 9, further comprising
at least one air inlet;
at least one air outlet; and
an aerosol forming chamber disposed between the at least one air inlet and the at least one air outlet,
wherein the aerosol forming chamber defines an air flow route from the at least one air inlet to the at least one air outlet via the aerosol forming chamber, and
wherein the air flow route passes through the interior passageway.

11. A cartridge, comprising:
an aerosol-forming substrate;
a vaporizer configured to heat the aerosol-forming substrate;
a capillary material configured to convey the aerosol-forming substrate towards the vaporizer by capillary action; and
a porous material between the capillary material and the vaporizer,
wherein the vaporizer is disposed inside a porous member, and
wherein a portion of the porous member disposed between the vaporizer and the capillary material forms the porous material.

12. The cartridge according to claim 11, wherein the aerosol generating device is electrically operated and the vaporizer comprises an electric heater configured to heat the aerosol-forming substrate, the electric heater being connectable to an electric power supply in the aerosol generating device.

13. The cartridge according to claim 11, wherein the porous material comprises a heat-resistant material.

14. The cartridge according to claim 12, wherein the electric heater is configured to reach a temperature of between 200 degrees Celsius and 440 degrees Celsius.

15. The cartridge according to claim 11, wherein the porous material is ceramic.

16. The cartridge according to claim 11, wherein the porous material and the capillary material comprise different materials.

17. The cartridge according to claim 11, wherein the vaporizer and the porous member are integrally formed.

18. The cartridge according to claim 11, further comprising a storage portion configured to store the aerosol-forming substrate, the storage portion being refillable.

19. The cartridge according to claim 11, further comprising a storage portion configured to store the aerosol-forming substrate, the storage portion comprising an interior passageway.

20. The cartridge according to claim 19, further comprising
at least one air inlet;
at least one air outlet; and
an aerosol forming chamber disposed between the at least one air inlet and the at least one air outlet,
wherein the aerosol forming chamber defines an air flow route from the at least one air inlet to the at least one air outlet via the aerosol forming chamber, and
wherein the air flow route passes through the interior passageway.

21. An aerosol generating system, comprising:
an aerosol generating device in cooperation with a cartridge, the cartridge or the aerosol generating device comprising an aerosol-forming substrate;
wherein the cartridge or the aerosol generating device comprises a vaporizer configured to heat the aerosol-forming substrate to form an aerosol;
wherein the cartridge or the aerosol generating device comprises a capillary material configured to convey the aerosol-forming substrate towards the vaporizer by capillary action; and
wherein the cartridge or the aerosol generating device comprises a porous material between the capillary material and the vaporizer,
wherein the vaporizer is disposed inside a porous member, and
wherein a portion of the porous member disposed between the vaporizer and the capillary material forms the porous material.

* * * * *